(12) United States Patent
Mordaunt

(10) Patent No.: US 9,579,235 B2
(45) Date of Patent: *Feb. 28, 2017

(54) LASER-ASSISTED THERMAL SEPARATION OF TISSUE

(71) Applicant: EXCEL-LENS, INC., Los Gatos, CA (US)

(72) Inventor: David H. Mordaunt, Los Gatos, CA (US)

(73) Assignee: EXCEL-LENS, INC., Los Gatos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/164,356

(22) Filed: May 25, 2016

(65) Prior Publication Data

US 2016/0262935 A1    Sep. 15, 2016

Related U.S. Application Data

(63) Continuation of application No. 14/853,433, filed on Sep. 14, 2015, now Pat. No. 9,351,877, which is a
(Continued)

(51) Int. Cl.
*A61B 18/18*   (2006.01)
*A61F 9/008*   (2006.01)
(Continued)

(52) U.S. Cl.
CPC .......... *A61F 9/00836* (2013.01); *A61B 18/20* (2013.01); *A61F 9/008* (2013.01);
(Continued)

(58) Field of Classification Search
CPC .. A61F 2009/00887; A61F 2009/00889; A61F 2009/0087
(Continued)

(56) References Cited

U.S. PATENT DOCUMENTS 3,971,382 A    7/1976  Krasnov
3,982,541 A    9/1976  L'Esperance, Jr.
(Continued)

OTHER PUBLICATIONS

Horiguchi, et al., "Staining of the Lens Capsule for Circular Continuous Capsulorrhexis in Eyes With White Cataract", Apr. 1998, pp. 535-537, Arch Ophthalmol, vol. 116, www.archophthalmol.com.
(Continued)

*Primary Examiner* — William Thomson
*Assistant Examiner* — John R Downey
(74) *Attorney, Agent, or Firm* — Innovation Counsel LLP

(57) ABSTRACT

A laser-assisted method for fully or partially separating tissue such as collagen containing tissue is provided. In one embodiment, the method pertains to a capsulorhexis whereby the laser-assisted method is applied to the lens capsule. A light-absorbing agent is added into or onto the tissue. A light beam with a wavelength capable of being absorbed by the light absorbing agent is then directed at the tissue to cause a thermal effect at the tissue following a predetermined closed curve with the goal to avoid irregularity or potential tears in the resulting rim of the tissue.

11 Claims, 4 Drawing Sheets

Related U.S. Application Data continuation of application No. 14/059,206, filed on Oct. 21, 2013, now Pat. No. 9,155,657, which is a continuation of application No. 13/854,490, filed on Apr. 1, 2013, now Pat. No. 8,562,596, which is a continuation of application No. 12/286,020, filed on Sep. 26, 2008, now Pat. No. 8,409,182.

(60) Provisional application No. 60/995,792, filed on Sep. 28, 2007.

(51) Int. Cl.
    *A61B 18/20*     (2006.01)
    *A61F 9/009*     (2006.01)

(52) U.S. Cl.
    CPC ............ *A61F 9/009* (2013.01); *A61F 9/0084* (2013.01); *A61F 9/00834* (2013.01); *A61F 2009/0087* (2013.01); *A61F 2009/00887* (2013.01); *A61F 2009/00897* (2013.01)

(58) Field of Classification Search
    USPC ........................................................ 606/4–6
    See application file for complete search history.

(56) References Cited

U.S. PATENT DOCUMENTS

| | | | |
|---|---|---|---|
| 4,367,744 A | 1/1983 | Sole | |
| 4,481,948 A | 11/1984 | Sole | |
| 4,907,586 A | 3/1990 | Bille et al. | |
| 5,261,923 A | 11/1993 | Soares | |
| 5,283,598 A | 2/1994 | McMillan et al. | |
| 5,296,787 A | 3/1994 | Albrecht et al. | |
| 5,346,491 A | 9/1994 | Oertli | |
| 5,350,374 A | 9/1994 | Smith | |
| 5,437,658 A | 8/1995 | Muller et al. | |
| 5,507,740 A | 4/1996 | O'Donnel, Jr. | |
| 5,520,679 A | 5/1996 | Lin | |
| 5,569,280 A | 10/1996 | Kamerling | |
| 5,620,435 A | 4/1997 | Belkin et al. | |
| 5,722,970 A | 3/1998 | Colvard et al. | |
| 5,798,349 A | 8/1998 | Levy et al. | |
| 5,860,994 A | 1/1999 | Yaacobi | |
| 5,873,883 A | 2/1999 | Cozean, Jr. et al. | |
| 5,958,266 A | 9/1999 | Fugo et al. | |
| 5,984,916 A | 11/1999 | Lai | |
| 6,010,497 A | 1/2000 | Tang et al. | |
| 6,063,073 A | 5/2000 | Peyman | |
| 6,159,205 A | 12/2000 | Herekar et al. | |
| 6,165,190 A | 12/2000 | Nguyen | |
| 6,171,336 B1 | 1/2001 | Sawusch | |
| 6,210,401 B1 | 4/2001 | Lai | |
| 6,280,470 B1 | 8/2001 | Peyman | |
| 6,325,792 B1 | 12/2001 | Swinger et al. | |
| RE37,504 E | 1/2002 | Lin | |
| 6,351,663 B1 | 2/2002 | Flower et al. | |
| 6,367,480 B1 | 4/2002 | Coroneo | |
| 6,520,955 B2 | 2/2003 | Reynard | |
| 6,533,769 B2 | 3/2003 | Holmen | |
| 6,575,962 B2 | 6/2003 | Hohla | |
| 6,607,527 B1 | 8/2003 | Ruiz et al. | |
| 6,673,067 B1 | 1/2004 | Peyman | |
| 7,014,991 B2 | 3/2006 | Buono | |
| 7,691,099 B2 | 4/2010 | Berry | |
| 8,409,182 B2 | 4/2013 | Mordaunt | |
| 8,562,596 B2 | 10/2013 | Mordaunt | |
| 2003/0212387 A1* | 11/2003 | Kurtz ...................... | A61F 9/008 606/4 |
| 2003/0213780 A1 | 11/2003 | Fugo et al. | |
| 2004/0206364 A1 | 10/2004 | Flower | |
| 2005/0173383 A1 | 8/2005 | Coccio et al. | |
| 2006/0195076 A1 | 8/2006 | Blumenkranz et al. | |
| 2007/0055156 A1 | 3/2007 | Desilets et al. | |
| 2007/0093868 A1 | 4/2007 | Fugo | |
| 2007/0121069 A1 | 5/2007 | Andersen et al. | |
| 2008/0281303 A1 | 11/2008 | Culbertson et al. | |
| 2014/0046310 A1 | 2/2014 | Mordaunt | |
| 2016/0000603 A1 | 1/2016 | Mordaunt | |

OTHER PUBLICATIONS

Haritoglou, et al., "An Evaluation of Novel Vital Dyes for Intraocular Surgery", Sep. 2005, pp. 3315-3322. Investigative Ophthalmology & Visual Science, vol. 46, No. 9.

* cited by examiner

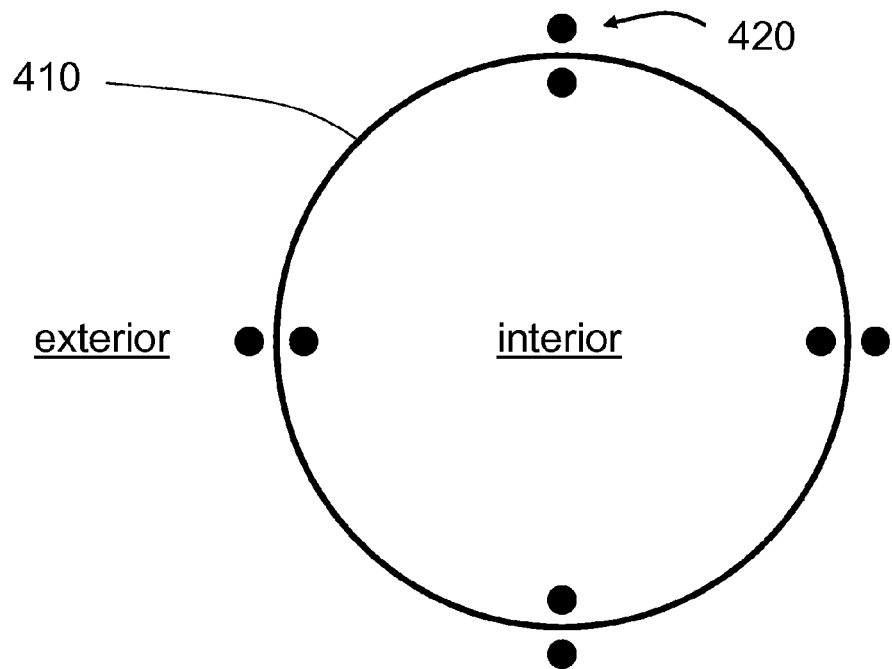
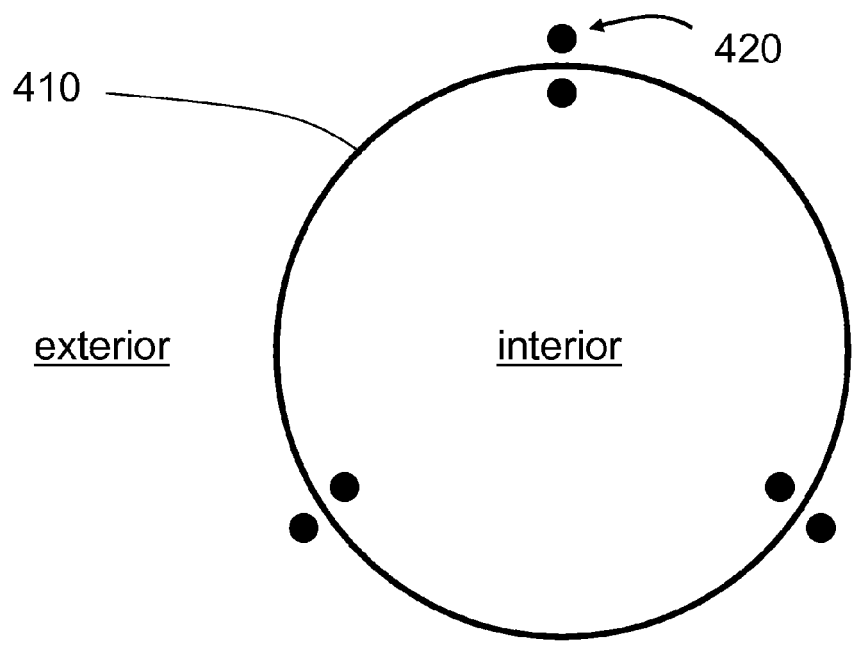

LASER-ASSISTED THERMAL SEPARATION OF TISSUE

CROSS REFERENCE TO RELATED APPLICATIONS

This application is a continuation of U.S. patent application Ser. No. 14/853,433 filed Sep. 14, 2015, which is a continuation of U.S. patent application Ser. No. 14/059,206 filed Oct. 21, 2013 (now U.S. Pat. No. 9,155,657), which is a continuation of U.S. patent application Ser. No. 13/854,490 filed Apr. 1, 2013 (now U.S. Pat. No. 8,562,596) which is a continuation of U.S. patent application Ser. No. 12/286,020 filed Sep. 26, 2008 (now U.S. Pat. No. 8,409,182), which claims priority from U.S. Provisional Patent Application 60/995,792, filed on Sep. 28, 2007, each of which is incorporated herein by reference in its entirety.

FIELD OF THE INVENTION

The present invention relates to surgeries and procedures for removing or separating tissue. In particular, the invention relates to methods and devices for performing a capsulorhexis.

BACKGROUND

Cataracts are a common cause for poor vision. They are the leading cause of blindness with a prevalence of over 20 M worldwide. In addition, there are at least 100 M eyes with cataracts causing visual acuity of less than 6/60 in meters (or 20/200 in feet). Cataract extraction is the most commonly performed surgical procedure in the world with estimates of 10 million cases worldwide and 2 million cases being performed annually in North America. There are three types of cataract extraction: intracapsular, small incision cataract and phacoemulsification.

Currently, intracapsular surgery is commonly performed in developing countries where there are less resources. In this procedure both the opacified natural lens and the lens capsule are removed together.

In small incision cataract surgery and phacoemulsification the opacified natural lens is removed while leaving the elastic lens capsule intact to allow implantation and retention of the intraocular lens (IOL). One of the more critical surgical components is the capsulorhexis.

Capsulorhexis is the incision in the lens capsule to permit removal of the lens nucleus and cortex. The lens capsule is a transparent, homogeneous basement membrane that is made up of collagen-like protein. It has elastic properties without being composed of elastic fibers. The capsule has a smooth surface contour except at its equator where the zonules attach.

Ideally the capsulorhexis creates a symmetric circular incision, centered about the optical axis and is sized appropriately for the IOL and patient's condition. The mechanical integrity around the newly formed incision edge needs to be sufficient to withstand the forces experienced during cataract extraction and IOL implantation. By maintaining integrity of the remaining capsule, the IOL haptics are located in proximity of the capsule equator to allow location of the IOL. Postoperatively the newly formed capsule rim hardens and the opening contracts providing further strength and structural support for the IOL to prevent dislocation and misalignment. Because of this postoperative contraction it is important that the opening diameter and the IOL optic diameter are purposefully mismatched, otherwise the resultant pressures may cause the IOL to be dislocated.

The current standard of care for capsulorhexis is Continuous Curvilinear Capsulorhexis (CCC). The concept of the CCC is to provide a smooth continuous circular opening through the anterior lens capsule for phacoemulsification and insertion of the intraocular lens minimizing the risk of complications including errant tears and extensions. Currently, the capsulorhexis is performed manually utilizing forceps or a needle. The technique is dependent on applying a shear force and minimizing in-plane stretching forces to manually tear the incision.

The size of the capsulorhexis is determined by technique, the zonules strength and IOL optic diameter. Zonular strength is assessed prior to capsulorhexis. If the zonules appear strong then the capsulorhexis diameter should measure about 4-5 mm being about 0.5 to 1.0 mm smaller than the IOL optic diameter and centered on the optical axis. This provides overlap with the IOL and some margin for error. If the assessment shows a generally loose lens diaphragm then the capsulorhexis should be made about 5 to 7 mm in diameter being about 0.5 to 1.0 mm larger than the IOL optic diameter, again centered on the optical axis. If the zonular strength assessment shows asymmetric weakness the capsulorhexis should still be 5 to 7 mm in diameter being 0.5 to 1.0 mm larger than the IOL optic diameter, but located off-center away from the possible dehiscence. This would allow the IOL optic to be aligned and centered up with the capsulorhexis when the haptics are oriented toward the quadrant of zonular weakness. Larger diameter capsulorhexis are more difficult because the steepness of the capsule wall increases towards the capsule equator, thus it is harder to limit the shear forces without stretching the capsule, and the probability increases of a rhexis escape, i.e., an errant tear.

Errant tears are radial rips and extensions of the capsulorhexis towards the equator, moreover if a zonular attachment is encountered the tear is sent directly out to the capsular fornix and possibly through to the posterior of the capsule. Furthermore, posterior capsule tears facilitate the nucleus being "dropped" into the posterior chamber resulting in further complications.

Further problems that may develop in capsulorhexis are related to inability of the surgeon to adequately visualize the capsule due to lack of red reflex, to grasp it with sufficient security, to tear a smooth symmetric circular opening of the appropriate size or technical difficulties related to maintenance of the anterior chamber depth after initial opening, small size of the pupil or the absence of a red reflex due to the lens opacity. Additional complications arise in older patients with weak zonules and very young children that have very soft and elastic capsules, which are very difficult to mechanically rupture.

Errant tears and other problems can be managed to some degree with the addition of dense viscoelastics and relaxing incisions to assist in stabilization of the capsule rim. If need be a two-stage capsulorhexis technique can be required to rescue a situation or for the formation of a second large capsulorhexis. Specifically, after creating an initial capsulorhexis, the anterior cortex is removed with aspiration and irrigation and the capsule is refilled with viscoelastic to stabilize the capsule and the capsulorhexis is enlarged by tearing a larger second capsulorhexis.

Further stress is applied to the capsulorhexis in phacoemulsification and implantation of the IOL, if the capsulorhexis is discontinuous or if the force is too great the capsulorhexis may cause a radial tear. This is dealt with as above. Furthermore if the posterior capsule integrity is damaged during the cataract surgery (i.e., a posterior capsule rent) dense viscoelastic is added to preserve its shape and a posterior capsulorhexis is performed, to salvage the integrity and strength of the capsule around its equator such that an IOL can be implanted.

Most current cataract surgeries are performed with the aid of phacoemulsification and typically include the following eighteen steps.

1. Pupil dilation
2. Local anesthesia
3. Placement of the lid speculum
4. Entry into the eye through a small incision (typically 2-3 mm in length, at the edge of the cornea)
5. Viscoelastic injected into the anterior chamber to maintain the volume and shape of the anterior chamber and cornea during the rest of the procedure
6. Zonule function test
7. Capsulorhexis
8. Hydrodissection intended to identify and soften the nucleus for the purposes of removal from the eye.
9 Hydro-delineation to increase the distance between the nucleus and the posterior capsule, thus providing a safety zone.
10. Nuclear cracking or chopping if needed
11. Ultrasonic with aspiration and irrigation used to sculpt and emulsification of the nucleus used to sculpt the relatively hard nucleus of the lens.
12. Aspiration of the residual soft cortex
13. Capsular polishing
14. Once the capsule is empty further addition of viscoelaslic to maintain the volume and shape of the capsule
15. Implantation of the artificial IOL
16. Centration of the IOL
17. Viscoelastic removal
18. Wound sealing/hydration (if needed)

Following cataract surgery there is a rapid 1-2 days response where the capsule hardens and the capsule contraction starts. This continues over a 4-6 week period where fibrosis of the capsulorhexis and IOL optic interface, and the haptic and capsule interfaces also occur. Even beyond one year the capsule continues to contract to a lesser degree, thus positioning the capsulorhexis is a critical factor in the long-term success.

Following cataract surgery one of the principal sources of visual morbidity is the slow development of opacities in the posterior lens capsule, which is generally left intact during cataract surgery as a method of support for the lens, and also as a means of preventing subluxation posteriorly into the vitreous cavity. It has been estimated that the complication of posterior lens capsule opacification occurs within 5 years of surgery with a 10% incidence. This problem is thought to occur as a result of epithelial and fibrous metaplasia along the posterior lens capsule centrally from small islands of residual epithelial cells left in place near the capsule equator. Q-switched Nd: YAG lasers are utilized to perform a non-invasive posterior capsulotomy to remove the opacification from the proximity of the optical axis.

Accordingly, there is a need in the art to provide new ophthalmic methods, techniques and apparatus to advance the standard of care for capsulorhexis.

SUMMARY

The present invention provides a laser-assisted method for separating tissue such as collagen-containing tissue. In one embodiment, the method is a capsulorhexis whereby the laser-assisted method is applied to the lens capsule.

A light-absorbing agent is added into or onto the tissue. A light beam with a wavelength capable of being absorbed by the light absorbing agent is then directed at the tissue to cause a thermal effect at the tissue. The light beam is: (i) characterized to remain at a sub-ablation level of the tissue or (ii) characterized to cause melting of the tissue. The light beam could either cause a full or partial separation, cutting or puncture of the tissue.

A predetermined closed curve is defined at the tissue. This curve defines an interior and an exterior. The light beam is directed at an initial and interior point of the predetermined closed curve. Once an initial puncture or partial/full separation has been achieved, the light beam continues and is further directed starting from the initial and interior point of the predetermined closed curve along the remaining path of the predetermined closed curve until at least the curve is closed. In one embodiment, the continued light beam ends at a final and interior point of the predetermined closed curve.

The initial and the continuing light beam(s) could be the same type of light beam or different types of light beams. In a preferred embodiment, the light beam is a laser beam from a CW laser. A CW laser is preferred for at least the continuing light beam to allow for a single pass along the curve to avoid irregularity or potential tears in the resulting rim of the tissue. The exterior path of the predetermined closed curve is preferably substantially circular or ellipsoidal in the application of a capsulorhexis but is not limited to these shapes in other applications.

Visualization patterns could be added and projected at the tissue which will aid in the procedure. The visualization patterns useful in this invention (i) are different from the predetermined closed curve or (ii) include at least 3 sets of dots, wherein each of the sets of dots is distributed along the interior-exterior border of the predetermined closed curve.

BRIEF DESCRIPTION OF THE DRAWINGS

The present invention together with its objectives and advantages will be understood by reading the following description in conjunction with the drawings, in which:

FIG. 2 also shows the contracted and shrunken ends 220-E and 220-I.

FIGS. 4A-4B show according to an embodiment of the present invention a visualization pattern 410, which preferably coincides with the perimeter of the closed curve (e.g. a circular pattern in this particular example). It is important to note that the visualization pattern 410 does not include the initial and end paths inside the interior area. FIGS. 4A-4B also show another visualization pattern with at least 3 sets of dots 420 to assist in focusing the light beam(s), whereby the sets of dots preferably are visualized along the interior-exterior border of the closed curve 310. FIG. 4A shows 4 sets of dots and FIG. 4B shows 3 sets of dots. Visualization patterns 410 and 420 could be used separately or together.

DETAILED DESCRIPTION

Figure 1:
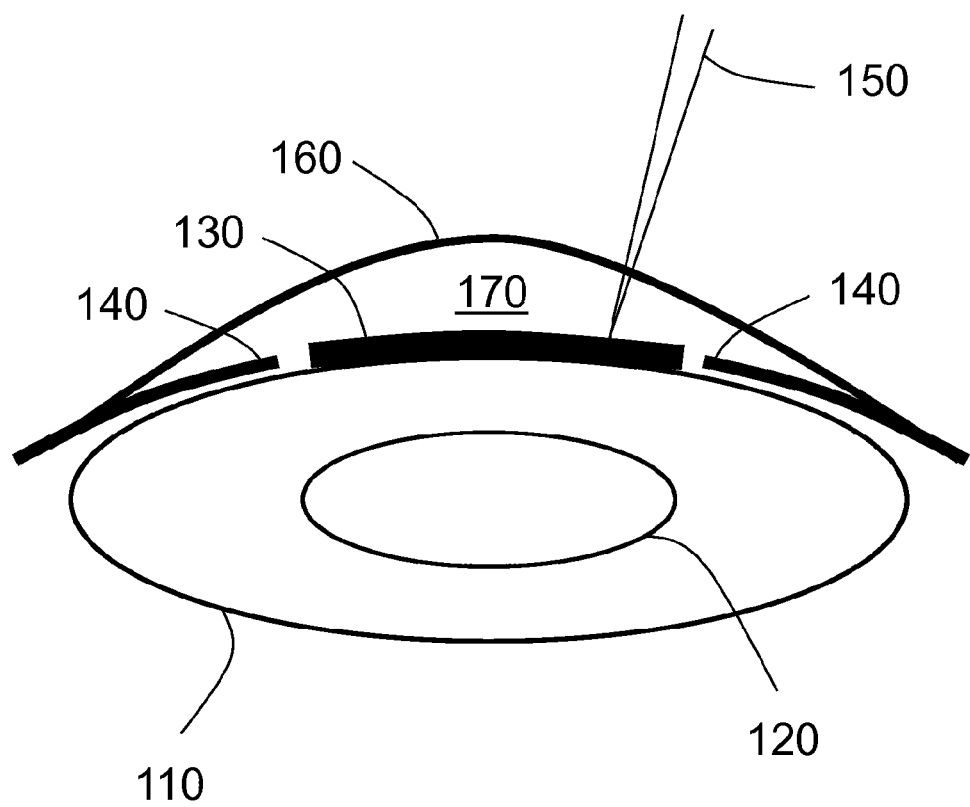
FIG. 1 shows according to an embodiment of the present invention a transverse plane view of some parts of the eye (lens capsule 110, IOL 120, dilated iris 140, cornea 160 and anterior chamber 170), a light absorbing agent 130 and a light beam 150.

FIG. 1 shows a transverse plane view of part of the eye. For the purposes of this invention the lens capsule 110 and the IOL 120 are shown including the iris 140 in dilated position. The anterior lens capsule is transparent and therefore does not readily absorb light. Prior attempts to use a laser to remove tissue or make a capsulorhexis in the lens capsule have utilized (i) photodisruption producing cavitation and/or mechanical shockwave, e.g. the Q-switched Nd:YAG lasers used for posterior capsulotomy, or (ii) plasma induced ablation e.g., the sub-picosecond lasers for 3-D scanned Capsulorhexis and nucleus fragmentation.

Figure 2:
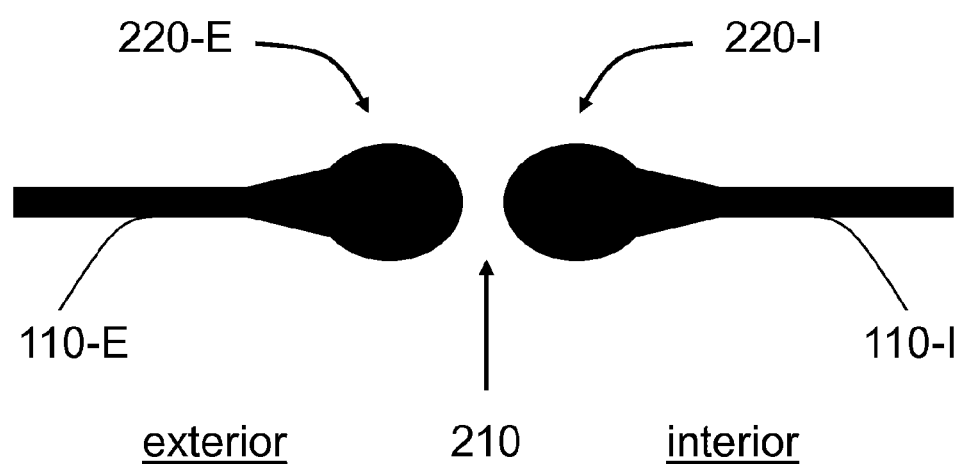
FIG. 2 shows according to an embodiment of the present invention a side view of the lens capsule 110 whereby the tissue (in this example lens capsule 110) has been separated at 210 into two parts, e.g. an exterior part 110-E and an interior part 110-I.

In this invention, a light absorbing agent 130 is added into or onto a layer of the anterior lens capsule 110. This agent could be a biocompatible agent (e.g. indocyanine green (ICG) or methyl blue), a dye, pigment, a nanoparticle, a carbon particle, or a like. Subsequently, a light beam 150, e.g. a laser, is directed to the anterior lens capsule. The directed light beam is absorbed by the light absorbing agent with the intent to cause a local thermal effect on the anterior lens capsule that yields a capsulorhexis. In other words, the wavelength, power, speed of light beam movement etc. of the light beam(s), should be selected so that it can be absorbed by the light absorbing agent to cause sufficient thermal energy adjacent or at the anterior lens capsule. Furthermore, the absorption of energy should be sufficient to cause a mechanical separation 210 effect at the anterior lens capsule (FIG. 2). In general, the light beam(s) are set to be at a sub-ablation level of the anterior lens capsule or are set to cause local melting or partial/full separation of the anterior lens capsule.

The lens capsule membrane contains collagen fibrils. As collagen is heated, it denatures, i.e. the triple-helix of collagen unwinds due to the disruption of hydrogen bonds between the adjacent alpha chains. Furthermore, collagen undergoes a transition from its crystalline helical structure to an amorphous structure and collagen shrinkage/contraction occurs (220-E, 220-I in FIG. 2). With the application of controlled heat by the directed light beam to the anterior lens capsule in the temperature range between 50 degrees Celsius and 150 degrees Celsius vaporization, membrane melting and shrinkage can occur. In another embodiment, the temperature range could be between 100 degrees Celsius and 120 degrees Celsius.

The capsulorhexis will be formed and the immediately adjacent tissue that forms the resultant rim will have the contracted amorphous collagen. This resulting rim is more elastic and resistant to tearing than the original membrane because it comprises this amorphous collagen and no additional mechanical forces have stressed/fractured the rim during this process. The shrunken and contracted ends 220E and 220-I separate (see 210) as a result of the directed light the anterior lens capsule 110 into the part that remains in the eye 110-E and the part that eventually is removed 110-I for the purposes of a capsulorhexis.

Figure 3:
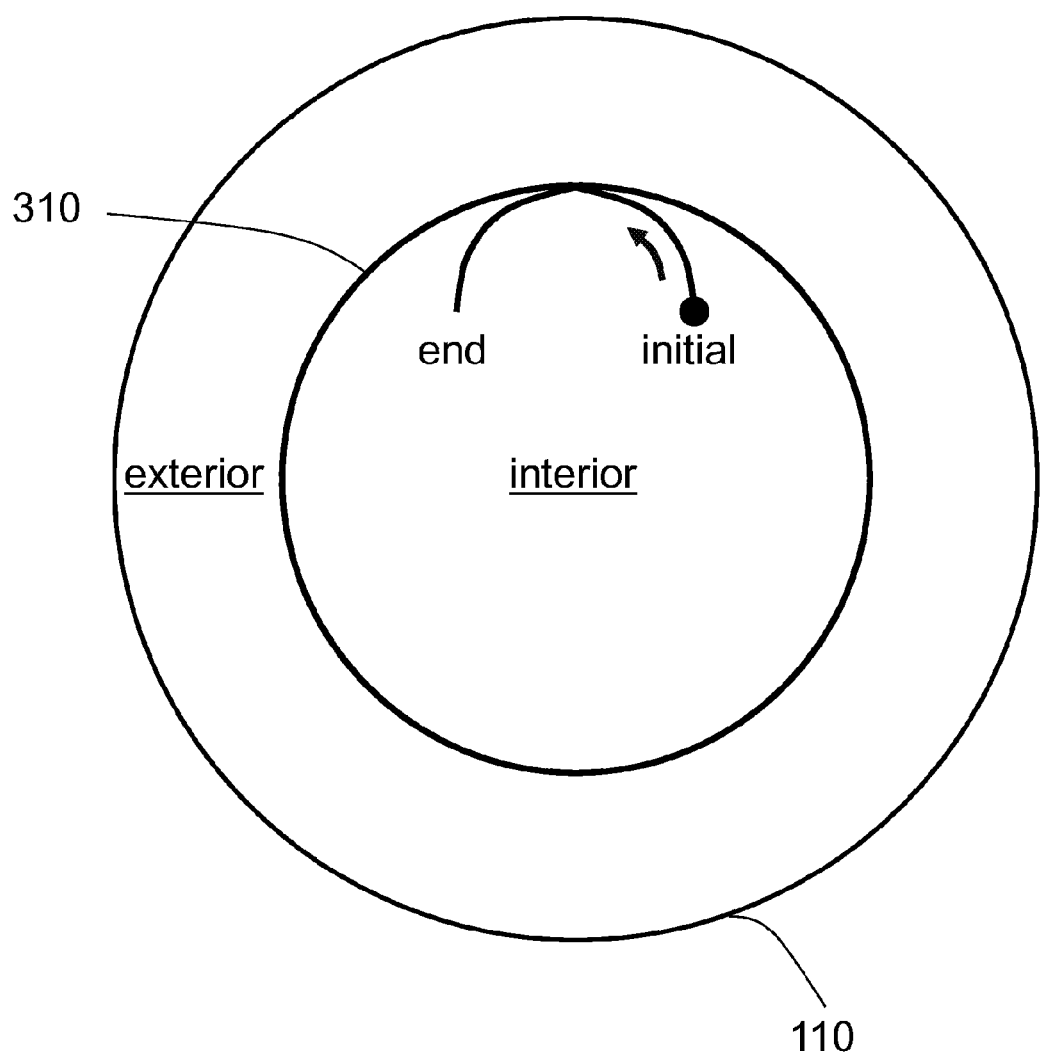
FIG. 3 shows according to an embodiment of the present invention a coronal plane view from an anterior direction of a tissue (in this example lens capsule 110) with a predetermined closed curve 310. It is important to note that the predetermined closed curve starts with an initial point inside of the closed curve. In one embodiment, the predetermined closed curve ends at any point where the curve becomes closed. In another embodiment, the predetermined curve ends with end-point within the interior area.

One of the key aspects of the invention is the pattern of the light beam directed at the anterior lens capsule (FIG. 3). FIG. 3 is a coronal plane view from an anterior direction of the lens capsule 110. A predetermined closed curve 310 is defined that will be used to direct the light beam(s) and perform the capsulorhexis. The closed curve 310 defines an interior and exterior area, whereby the interior area is enclosed by the closed curved 310 as shown in FIG. 3. The exterior area is anything outside the circumference of the closed curve 310. The predetermined closed curve distinguishes an initial starting point (initial) located in the interior area. Optionally the predetermined closed curve also includes an ending point (end) located in the interior area. The predetermined closed curve can be (pre)-programmed and added to the laser and optical system used for the performance of the capsulorhexis.

During execution, a light beam is directed to the initial point on the closed curve 310. The selection of the position of the initial point is to create an initial starting hole, puncture or separation in the anterior lens capsule while staying clear from the ultimate position of the rim of curve 310 upon capsulotomy. Since the initial point is inside the closed curve it avoids irregularity or potential tears in the resulting rim of the remaining anterior lens capsule (i.e. 220-E).

Once the initial point is created by the light beam and according to one embodiment, the light beam is directed from the initial point of the predetermined closed curve and continues (in the direction of the arrow and in this example counterclockwise) along the pattern of the predetermined closed curve until at least the curve is closed. In one embodiment, this endpoint could be at end as shown in FIG. 3 i.e. at the interior part of the closed curve again to avoid irregularity or potential tears in the resulting rim of the remaining anterior lens capsule or in another embodiment at any point once the curve is closed at the border of the interior/exterior area. For the purposes of a capsulorhexis, the shape of the exterior perimeter of the closed curve is preferably substantially circular or ellipsoidal.

The light beam at the initial point and the continued light beam along the curve path could be the same light beam or could be different light beams either with the same or different characteristics or parameters. The initial point could also be seen as an initial puncture before following the path of the curve and, according to this example, the initial light beam could then be different from the continuing light beam.

In one embodiment, for example, but not limiting to the scope of the invention, the initial light beam or puncture could have the following parameters:
  Speed of movement: 0 to 10 mm/second, basically dwelling on one location or oscillating a small region for a time of about 0.25 to 3 sec.
  Diameter of light beam on the surface: 50-600 microns.
  Power of light beam dependent on the light absorbing agent, but ideally less than 1000 mW.

In one embodiment, for example, but not limiting to the scope of the invention, the continuing light beam which at least closes the curve could have the following parameters:
  Speed of movement: 0.25 to 10 mm/second, preferably in a single pass along the curve.
  Diameter of light beam on the surface: 50-600 microns.
  Power of light beam dependent on the light absorbing agent, but ideally less than 1000 mW.

In a preferred embodiment, for example, but not limiting to the scope of the invention, the continuing light beam which at least closes the curve could have the following parameters:
  Speed of movement: 0.5 to 3 mm/second, preferably in a single pass along the curve.

Diameter of light beam on the surface: 100-300 microns.

Power of light beam dependent on the light absorbing agent, but ideally less than 600 mW.

The continuing light beam is preferably accomplished in a single pass to provide as much consistency in the rim pattern as possible with the rim being formed with the same or at least similar) thermal conditions. The single pass is also important to ensure completion of the capsulorhexis even if there is slight movement of the eye relative to the trajectory. Preferably and in particular for the continuing light beam a CW laser is used. However, a high-frequency pulsed (>1 KHz) pulsed laser, e.g. a subpico Q-switched laser could also be used. In one embodiment, the wavelength could be in the infrared to near infrared region of the spectrum, thus it would be near invisible to the patient, providing minimal irritation.

A visible aim beam or pattern(s) could be present to project the laser-cutting or laser-separating trajectory or to project at least part of the closed curve on the anterior lens capsule surface. The visualization patterns are useful to bring the laser into focus on the lens capsule surface and to allow the physician to select the location and size of the capsulorhexis. To get the visible aim beam into focus is often hard especially for a ring, since you are looking for a sharp edge on the aim beam or its smallest width of the line.

To assist focusing the method described herein could be extended by projecting a visualization pattern 410, which preferably coincides with the perimeter of the closed curve (e.g. a circular pattern in this particular example) (FIG. 4). In other words, a key aspect of this invention is that visualization pattern 410 is different from the pattern of the closed curve 310 (i.e. 410 does not include the initial and end paths in the interior side of the closed curve). FIG. 4 also shows another visualization pattern with at least 3 sets of dots 420 to assist in focusing the light beam(s), whereby the set of dots preferably are visualized along the interior-exterior border of the closed curve 310. Such a pattern of discrete dots 420 is far easier to focus and or orienting the eye of the patient. Pattern 410 and 420 could be used separately or combined.

In one embodiment, for example, but not limiting to the scope of the invention, the visualization light beam could have the following parameters:

Speed of movement: greater than 450 mm/second.

Diameter of light beam on the surface: 50-600 microns

Power of light beam is dependent on the light absorbing agent, with an average power of less 1 mW.

Wavelength is in the visible spectrum.

As one of ordinary skill in the art will appreciate, various changes, substitutions, and alterations could be made or otherwise implemented without departing from the principles of the present invention. For example, in one variation the methods described herein could be varied from the application of a capsulorhexis to thermally cutting or partially/fully separating tissue or collagen-containing material. In yet another variation, the laser-assisted capsulorhexis does not penetrate the full thickness of the anterior lens capsule, but there is a groove in the capsule surface. The full thickness capsulorhexis could then be completed manually with a CCC with the groove guiding the manual tear. In still another variation, additional methods for fixating the eye could be added for example by placing a surgical contact lens on the eye. This will minimize the eye motion. Moreover, the scanning device or any other device could hold the contact lens thus restricting the eye motion further. The use of a contact lens could also increase the ability to focus the light with a great numerical aperture, allowing more accurate focusing on the specific target tissue and reduce or eliminate potential light beam exposure to the retina, cornea, fovea posterior capsule and cataractus lens and therewith less of a disturbance/irritation to the patient. Accordingly, the scope of the invention should be determined by the following claims and their legal equivalents.

What is claimed is:

1. A device for thermally separating tissue in the anterior lens capsule of an eye in a procedure creating an opening in the anterior lens capsule, the device comprising:

a laser device programmed to direct a treatment laser beam along a predetermined closed curve on the anterior lens capsule in a single pass starting at an initial point interior to the closed curve, then along the closed curve, and then to a final point interior to the closed curve;

wherein the treatment laser beam diameter at the anterior lens capsule is 50 microns to 300 microns; and wherein the treatment laser beam power and wavelength at the anterior lens capsule are such that the treatment laser beam is absorbed by a light absorbing agent in or on the anterior lens capsule to cause a local temperature increase at the anterior lens capsule along the closed curve of between 50 degrees Celsius and 150 degrees Celsius without ablation of the anterior lens capsule, thereby separating the anterior lens capsule along the closed curve to form an area of anterior lens capsule tissue inside the closed curve and an area of anterior lens capsule tissue outside the closed curve, the lens capsule tissue outside the closed curve defining the boundary of the opening in the anterior lens capsule.

2. The device of claim 1, wherein the light absorbing agent is added to the anterior lens capsule.

3. The device of claim 1, wherein the treatment laser beam is a continuous wave laser beam.

4. The device of claim 1, wherein the closed curve is circular or elliptical.

5. The device of claim 1, wherein absorption of the treatment laser beam by the light absorbing agent causes a temperature increase at the anterior lens capsule along the closed curve of between 100 degrees Celsius and 120 degrees Celsius.

6. The device of claim 1, comprising a laser device programmed to direct a visible laser beam along a visualization pattern on the anterior lens capsule to assist a user in selecting the location and size of the opening to be created in the anterior lens capsule.

7. The device of claim 1, in combination with a surgical contact lens that increases the numerical aperture with which the laser beam is focusable onto the anterior lens capsule thereby reducing exposure of the retina and the fovea of the eye to the laser beam.

8. The device of claim 1, wherein absorption of the laser beam thermally transitions collagen in the anterior lens capsule tissue from a helical structure to an amorphous structure resulting in shrinkage or contraction of the tissue along the closed curve.

9. The device of claim 6, wherein the visualization pattern differs from the closed curve.

10. The device of claim 6, wherein the visualization pattern comprises discrete dots assisting in focusing the treatment laser beam.

11. The device of claim 4, wherein a diameter of the closed curve is 4 millimeters to 5 millimeters.

\* \* \* \* \*